(12) United States Patent
Lee et al.

(10) Patent No.: US 11,370,989 B2
(45) Date of Patent: Jun. 28, 2022

(54) FRAGRANT MATERIAL HAVING LONG-LASTING FRAGRANCE AND METHOD FOR PREPARING SAME

(71) Applicant: MASSCON CO., LTD., Gyeonggi-do (KR)

(72) Inventors: Yongeui Lee, Gyeonggi-do (KR); Minyoung Cheong, Gyeonggi-do (KR)

(73) Assignee: MASSCON CO., LTD., Gyeonggi-do (KR)

( * ) Notice: Subject to any disclaimer, the term of this patent is extended or adjusted under 35 U.S.C. 154(b) by 26 days.

(21) Appl. No.: 16/621,480

(22) PCT Filed: Jun. 21, 2018

(86) PCT No.: PCT/KR2018/007047
§ 371 (c)(1),
(2) Date: Dec. 11, 2019

(87) PCT Pub. No.: WO2018/236170
PCT Pub. Date: Dec. 27, 2018

(65) Prior Publication Data
US 2020/0291325 A1   Sep. 17, 2020

(30) Foreign Application Priority Data
Jun. 21, 2017 (KR) .................. 10-2017-0078412

(51) Int. Cl.
| | | |
|---|---|---|
| *A61K 8/00* | (2006.01) | |
| *A61K 8/18* | (2006.01) | |
| *A61Q 13/00* | (2006.01) | |
| *C11B 9/00* | (2006.01) | |
| *C08K 3/34* | (2006.01) | |
| *C08K 3/36* | (2006.01) | |
| *C08K 3/30* | (2006.01) | |

(52) U.S. Cl.
CPC ................ *C11B 9/00* (2013.01); *C08K 3/346* (2013.01); *C08K 3/36* (2013.01); *C08K 2003/3045* (2013.01); *C08K 2201/007* (2013.01)

(58) Field of Classification Search
CPC .. C11B 9/00; C08K 9/12; C08K 3/346; C08K 3/36; C08K 1/00; C08K 2201/0007; C08K 2003/3045; A61L 9/04
USPC ....................................... 512/2, 1
See application file for complete search history.

(56) References Cited

U.S. PATENT DOCUMENTS

| 5,336,665 A * | 8/1994 | Garner-Gray ........ A61K 8/0241 510/101 |
|---|---|---|
| 2007/0003492 A1 | 1/2007 | Kitahata et al. |
| 2014/0127145 A1* | 5/2014 | Deckner ................. C01B 33/18 424/57 |

FOREIGN PATENT DOCUMENTS

| JP | 2000239694 | * | 9/2000 | |
|---|---|---|---|---|
| KR | 10-1993-0008123 A | | 5/1993 | |
| KR | 10-0851730 B1 | | 8/2008 | |
| KR | 10-2011-0129505 A | | 12/2011 | |
| KR | 1020110129505 | * | 12/2011 | |
| KR | 20120083737 | * | 7/2012 | |
| KR | 10-1375125 B1 | | 3/2014 | |
| KR | 101375125 | * | 3/2014 | |
| WO | WO-2008149232 A2 | * | 12/2008 | ............. A23B 7/154 |

OTHER PUBLICATIONS

Kimura et al, JP 2000-239694 Machine Translation, Sep. 5, 2000 (Year: 2000).*
Jong, KR 1020110129505 Machine Translation, Dec. 2, 2011 (Year: 2011).*
Park et al, KR 20120083737 Machine Translation, Jul. 26, 2012 (Year: 2012).*
Ro et al, KR 101375125 Machine Translation, Mar. 18, 2014 (Year: 2014).*
International Search Report for Application No. PCT/KR2018/007047 dated Oct. 25, 2018.

* cited by examiner

*Primary Examiner* — Jessica Whiteley
(74) *Attorney, Agent, or Firm* — Christensen, Fonder, Dardi & Herbert PLLC; Diane E. Bennett; Peter S. Dardi

(57) ABSTRACT

The present invention relates to a fragrant material containing aromatic essential oil for improving the retention of the smell and intensity of aroma of aromatic essential oil, and to a method for preparing the same. The fragrant material having long-lasting fragrance according to an embodiment of the present invention contains aromatic essential oil and porous silica loading the aromatic essential oil and having controlled hydrophilicity or hydrophobicity of a surface thereof, wherein the required hydrophilic-lipophilic balance (rHLB) of the aromatic essential oil and the O/C ratio in the porous silica satisfy 0.9≤required hydrophilic-lipophilic balance (rHLB) of aromatic essential oil/(O/C ratio of porous silica)≤2.9.

19 Claims, 7 Drawing Sheets porous silica

FRAGRANT MATERIAL HAVING LONG-LASTING FRAGRANCE AND METHOD FOR PREPARING SAME

CROSS REFERENCE TO RELATED APPLICATIONS

This application is a National Stage filing of PCT Application No. PCT/KR2018/007047 filed Jun. 21, 2018, entitled "FRAGRANT MATERIAL HAVING LONG-LASTING FRAGRANCE AND METHOD FOR PREPARING SAME", which claims priority to Korean Patent Application No. 10-2017-0078412 filed Jun. 21, 2017, both of which are incorporated herein by reference.

BACKGROUND OF THE INVENTION

1. Field of the Invention

The present invention relates to a fragrant material including aromatic essential oil for improving the retention of smell and intensity of aroma of aromatic essential oil and a method for preparing the same.

2. Description of the Related Art

Aroma is widely used in almost all household goods such as fragrances, detergents, cosmetics, food, etc., and it can be divided into artificial synthetic aroma and natural aroma according to the manufacturing (extraction) method. Almost all household goods used today contain artificial synthetic aroma. The artificial synthetic aroma is known to contain harmful substances such as volatile organic compounds (VOCs), methyl isothiazoline, chloroxylenol or naphthalene paradichlorobenzene. Harmfulness issues about fragrance products have emerged seriously and have caused alarm to product users.

Essential oils are known to be harmless to humans because they are extracted from natural plants, and when used properly, to have therapeutic effects such as stimulation promoting action, sedative action, metabolic function promoting action and immune function enhancing effect. Therefore, when they replace artificial synthetic aroma, they can provide a lot of benefits to users. However, they have extremely limited range of use in terms of space and time and they are applied only to premium products due to the high price.

In terms of materials, aromatic essential oil refers to natural oil extracted from flowers, buds, leaves, stems, shells, roots, etc. of aromatic plants grown in nature or grown organically.

The main components of the essential oil are monoterpene and sesquiterpene hydrocarbons polymerized by isoprene and terpene compounds such as alcohols, aldehydes, ketones and esters derived therefrom. Currently there are more than 1,500 kinds of essential oils, of which about 200 kinds of essential oils are used as natural essential oils. Such essential oils are known to be free from artificial synthetic substances that are harmful to the human body and to have a good aroma. In addition, it is known to have excellent disinfection and antiseptic effects and have vitality and healing power when used properly. These essential oils are used alone or in mixtures of some essential oils or are diluted in carrier oils (jojoba, basil, coconut, almonds, hazelnut oil, etc.) to be used for aromatherapy.

Table 1 summarizes the representative essential oils and the efficacy.

TABLE 1

Type and efficacy of representative aromatic essential oils

| Essential oil | Efficacy |
|---|---|
| Lavender | Sedation, stress relief, good sleep help, headache/neuralgia/physiological pain relief, etc. |
| Cinnamon Leaf | Providing mental and physical energy, promoting blood circulation, alleviating infectious symptoms, and treating athlete's foot, etc. |
| Tea Tree | Diversion, anti-bacterial/fungal/viral, enhanced immunity, bactericidal action, etc. |
| Cedar Wood | Relief of tension/anxiety, sedation, sterilization, insect resistance, etc. |
| Orange | Antidepressant action, anti-inflammatory action, antibacterial, antispasmodic, anti-fungal, etc. |
| Eucalyptus | Antiseptic, antibacterial, deodorant, antipyretic, antispasmodic, blood purification, antiviral, etc. |
| Bergamot | Diversion, sedation and annoyance relief, antiseptic, inflammation relief, etc. |
| Lemon | Diversion, appetite suppression, headache relief, antibacterial, flu treatment, skin disease relief, etc. |
| Lime | Diversion, promoting digestion, increasing appetite, antipyretic, cough relief, etc. |
| Mandarin | Reducing anxiety, alleviating insomnia, promoting digestion, increasing appetite, promoting skin regeneration, etc. |
| Myrrh | Antiseptic effect, rejuvenation, cold/bronchitis relief, skin activity, etc. |
| Neroli | Mental and physical relaxation, mind calming, sleep help, stress relief, etc. |
| Niaouli | Improving concentration, strengthening immunity, sterilizing and disinfection action, etc. |
| Peppermint | Diversion, Improving concentration, nausea/vomiting relief, etc. |
| Pine | Diversion, sterilizing and disinfection effect, infection prevention, pain relief, etc. |
| Rosemary | Memory, concentration strengthening, vitality, promoting blood circulation, pain relief, etc. |
| Chamomile | Stress relief, sleep induction, pain relief, etc. |
| Ylang Ylang | Sedation/exciting balance help, good sleep help, disinfection, etc. |
| Neem | Skin trouble soothing, anti mold, pest control, etc. |
| Frankincense | Alleviating anxiety/relaxation, lung cleansing, cough/asthma relief, etc. |
| Benzoin | Alleviating anxiety/relaxation, cold/cough relief, etc. |
| Helichrysum | Increasing immunity, anti-allergy, anti-inflammatory, antiseptic, etc. |
| Phytoncide | Forest bath effect, odor removal/deodorant, antibacterial, insect repellent, etc. |

In general, a variety of volatile aroma components are mixed in the aromatic essential oil and the type of aroma is determined by the type of the contained volatile aroma and the composition ratio thereof. Since essential oils are in the liquid state, it is difficult to control the concentration or the releasing rate of aroma. In particular, in case of long-term releasing, the components having a relatively high volatility evaporate preferentially, thereby changing the aroma ratio of remaining essential oils and causing different aroma characteristics from the initial aroma.

Thus, studies have been conducted to improve the concentration and the releasing rate of aroma of essential oils and the retention of aroma intensity, and to facilitate fragrance emittance in various environments. Attempts have been made to microencapsulate the liquid essential oils in order to enhance the retention of aroma intensity and to confine aroma in porous materials. However, development maturity is not enough to be commercialized.

Meanwhile, such essential oils are also known to be effective in improving behavioral disorders, anger control, skin trouble relief or fleas and pest control in animals, and thus their application to aromatherapy for animals is attracting attention.

However, it is known that animals are sensitive to aroma about 50 to 100 times compared to humans, and that some kinds of aromas, which are harmless to the human body, can be fatal to the health of animals. Therefore, great care is required in their use.

Aromatic essential oil is usually used to apply or spray directly to the skin of humans or animals, or to inhale aroma vapor into the nose. In general, as a method of inhaling aroma vapor, there is used a method of putting oil in a bottle and diffusing the aroma into air using a diffuser, and in some cases, to dropping and mixing a small amount of oil into a solidified carrier such as gypsum and candle to use indoors.

In case of using oil in a bottle, if the bottle is dropped, the bottle may be broken and the oil may leak, resulting in a risk factor for children or animals. In case of candles, there is a fire risk. As such, in using the essential oil in real life, there are severe space and time constraints, for example a need for a guardian, and thus the use thereof is limited.

SUMMARY OF THE INVENTION

As mentioned above, aromatic essential oil contains various kinds of components, and the contained components determine hydrophilic or hydrophobic properties of the essential oil. Therefore, in order to completely load essential oil in a carrier and ensure loading stability, it is important to control hydrophilicity or hydrophobicity of the carrier.

The hydrophilicity or hydrophobicity of the carrier can be controlled by the control of functional groups present on the surface of the carrier. The control of these functional groups is possible through atmospheric heat treatment, chemical reaction or adsorption/desorption of the carrier.

According to one embodiment of the present invention, it is an object of the present invention to provide an essential oil fragrant material (primary carrier) which can overcome the above-mentioned space and time constraints and enhance the ease of use, by loading various kinds of liquid aroma components with controlling hydrophilicity or hydrophobicity of the surface of porous silica to prepare a fragrant material having long-lasting fragrance in which a solid form of material (primary carrier) is loading a liquid form of essential oil.

According to another embodiment of the present invention, it is an object of the present invention to provide various types of essential oil products that can further control the releasing concentration and time of aroma, eliminate potential risk factors (fire, bottle breakage, etc.) of the existing usage, and impart the convenience of use such as portability, by mixing or coating the essential oil fragrant material (primary carrier) with a polymer material such as silicone, rubber, plastic and urethane, clay or gypsum to provide a function of a dual carrier.

In addition, it is an object of the present invention to provide various applications for pets having long-lasting fragrance that can be used without a guardian and used safely and conveniently not only indoors but also outside, by adjusting the concentration and retention of aroma for pets that are very sensitive to aroma.

The object of the present invention is not limited to those mentioned above, and other objects not mentioned will be clearly understood by those skilled in the art from the following description.

In order to solve the above technical problems, according to one embodiment of the present invention, the fragrant material having long-lasting fragrance comprises an aromatic essential oil, and porous silica for loading the aromatic essential oil, the porous silica having a surface with controlled hydrophilicity or hydrophobicity, wherein a required hydrophilic-lipophilic balance (rHLB) of the aromatic essential oil and an atomic ration between oxygen and carbon (O/C ratio) in the porous silica may satisfy the following condition:

0.9≤required hydrophilic-lipophilic balance (rHLB) of aromatic essential oil/(O/C ratio of porous silica)≤2.9.

The porous silica may be heat-treated under an atmosphere containing at least one of oxygen and water vapor.

The heat-treating may comprise the steps of: injecting the porous silica into a heating furnace; heat-treating for about 1 hour to 3 hours while maintaining the temperature of the heating furnace at about 100 to 550° C.; and cooling the heat-treated porous silica to 25° C.

The fragrant material having long-lasting fragrance according to one embodiment of the present invention may further comprise an additional carrier formed of at least one of a polymer material, clay and gypsum.

In addition, the additional carrier may be mixed with the porous silica or coated on the porous silica.

In addition, the fragrant material having long-lasting fragrance according to one embodiment of the present invention may be formed by mixing or coating the porous silica with the additional carrier, and then curing or drying according to a predetermined design.

The polymer material may be at least one of silicone, rubber, plastic, urethane, and a combination thereof.

According to another embodiment of the present invention, a fragrant product for pets having long-lasting fragrance may comprise an aromatic essential oil; porous silica for loading the aromatic essential oil, the porous silica having a surface with controlled hydrophilicity or hydrophobicity; and an additional carrier formed of at least one of a polymer material, clay and gypsum, the additional carrier being mixed with the porous silica or coating the porous silica, wherein the fragrant product for pets may be formed by mixing the porous silica loading the essential oil with the additional carrier or coating the porous silica with the additional carrier, and then curing or drying according to a predetermined design.

The porous silica may be heat-treated under an atmosphere containing at least one of oxygen and water vapor.

The heat-treating may comprise the steps of: injecting the porous silica into a heating furnace; heat-treating for about 1 hour to 3 hours while maintaining the temperature of the heating furnace at about 100 to 550° C.; and cooling the heat-treated porous silica to 25° C.

The polymer material may be at least one of silicone, rubber, plastic, urethane, and a combination thereof.

According to another embodiment of the present invention, the fragrant product having long-lasting fragrance may comprise an aromatic essential oil, porous silica for loading the aromatic essential oil, the porous silica having a surface with controlled hydrophilicity or hydrophobicity; and purified water to be mixed or dispersed with the aromatic essential oil loaded in the porous silica.

The required hydrophilic-lipophilic balance (rHLB) of the aromatic essential oil and the O/C ratio in the porous silica may satisfy the following condition:

0.9≤required hydrophilic-lipophilic balance (rHLB) of aromatic essential oil/(O/C ratio of porous silica)≤2.9.

The porous silica may be heat-treated under an atmosphere containing at least one of oxygen and water vapor.

The heat-treating may comprise the steps of: injecting the porous silica into a heating furnace; heat-treating for about 1 hour to 3 hours while maintaining the temperature of the heating furnace at about 100 to 550° C.; and cooling the heat-treated porous silica to 25° C.

The fragrant product having long-lasting fragrance according to another embodiment of the present invention may further comprise an additional carrier formed of at least one of a polymer material, clay and gypsum.

The polymer material may be at least one of silicone, rubber, plastic, urethane, and a combination thereof.

In addition, the additional carrier may be mixed with the porous silica or coated on the porous silica.

The fragrant product having long-lasting fragrance according to another embodiment of the present invention may be at least one of an aromatic spray, an aromatic liquid product, a detergent/cleansing, a body care product and a hair care product.

According to an embodiment of the present invention, a method of preparing a fragrant material having long-lasting fragrance may comprise the steps of: heat-treating porous silica to adjust hydrophilicity or hydrophobicity of a surface thereof, and mixing aromatic essential oil with the heat-treated porous silica to load therein, wherein the required hydrophilic-lipophilic balance (rHLB) of the aromatic essential oil and the O/C ratio in the porous silica may satisfy the following condition:

0.9≤required hydrophilic-lipophilic balance (rHLB) of aromatic essential oil/(O/C ratio of porous silica)≤2.9.

The heat-treating may proceed under an atmosphere containing at least one of oxygen or water vapor.

The heat-treating may comprise the steps of: injecting the porous silica into a heating furnace; heat-treating for about 1 hour to 3 hours while maintaining the temperature of the heating furnace at about 100 to 550° C.; and cooling the heat-treated porous silica to 25° C.

The method of preparing a fragrant material having long-lasting fragrance according to an embodiment of the present invention may further comprise a step of mixing or coating the porous silica loading the essential oil with an additional carrier formed of at least one of a polymer material, clay and gypsum.

The polymer material may be at least one of silicone, rubber, plastic, urethane, and a combination thereof.

The method of preparing a fragrant material having long-lasting fragrance according to an embodiment of the present invention may further comprise a step of producing fragrant applications by mixing or coating the porous silica with the additional carrier, and then curing or drying according to a predetermined design.

The essential oil may be a single essential oil extracted from lavender, cinnamon leaf, tea tree, cedar wood, orange, eucalyptus, bergamot, lemon, lime, mandarin, myrrh, neroli, niaouli, peppermint, pine, rosemary, chamomile, ylang-ylang, neem, frankincense, benzoin or helichrysum, or a mixture containing at least one of these essential oils, or may be essential oil in carrier oil (jojoba, basil, coconut, almonds, hazelnut oil, etc.).

Effect of the Invention

The fragrant material having long-lasting fragrance according to an embodiment of the present invention can load various kinds of aroma components and regulate not only the retention of smell but also the intensity and releasing time of aroma, by using porous silica having controlled hydrophilicity or hydrophobicity as a carrier.

In addition, according to another embodiment, it is possible to provide a method applicable to various applications that can further control the concentration and releasing time of aroma, by mixing or coating with a polymer material such as silicone, rubber, plastic and urethane, clay or gypsum to prepare a dual carrier.

In addition, the fragrant material having long-lasting fragrance according to other embodiment of the present invention can be widely applicable to household goods or cosmetics such as an aromatic spray, an aromatic liquid product, a detergent/cleansing, a body product and a hair product, when mixing with or dispersing in purified water, etc.

The effects of the present invention are not limited to those mentioned above, and other effects, which are not mentioned above, will be clearly understood by those skilled in the art from the following description.

DETAILED DESCRIPTION OF THE INVENTION

The objects and effects of the present invention and the technical configurations for achieving them will be apparent with reference to the embodiments described below in detail with the accompanying drawings. In the following description of the present invention, detailed description of known functions will be omitted if it is determined that it may obscure the gist of the present invention.

However, the present invention is not limited to the embodiments disclosed below, but may be implemented in various forms. The present embodiments are merely provided to complete the disclosure of the present invention and to fully inform the scope of the invention to those skilled in the art, and the present invention is only defined by the scope of the claims. Therefore, the definition should be made based on the contents throughout the specification.

Throughout the specification, when a part is said to "comprise" or "include" a certain component, it means that it can further include other components, without excluding the other components unless otherwise stated.

Hereinafter, a fragrant material having long-lasting fragrance loading aromatic essential oil according to an embodiment of the present invention will be described in detail.

Figure 1A:
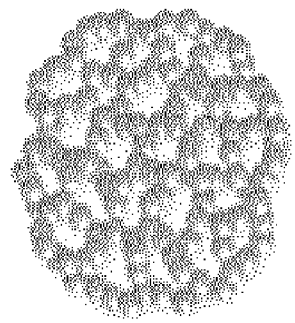
FIG. 1a is a schematic diagram of porous silica which is a carrier for essential oil according to an embodiment of the present invention and FIG. 1b is a schematic diagram of a fragrant material including the aromatic essential oil loaded on the porous silica.
Figure 1B:
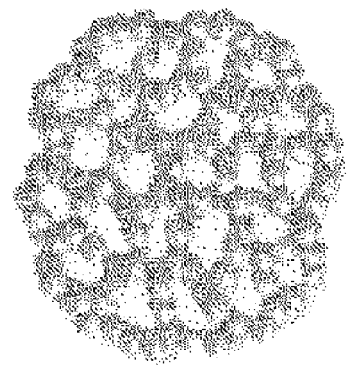
Figure 2:
FIG. 2 shows the types of essential oils and the chemical structural formula and the required hydrophilic-lipophilic balance (rHLB) of the main components included in each essential oil. The rHLB of essential oil shown in FIG. 2 is a literature value, and may vary according to a measurement method.

FIG. 1a is a schematic diagram of porous silica which is a carrier loading aromatic essential oil according to an embodiment of the present invention, FIG. 1b is a schematic diagram of a fragrant material including the aromatic essential oil loaded on the porous silica, and FIG. 2 shows the types of essential oils and the chemical structural formula and the required hydrophilic-lipophilic balance (rHLB) of the main components included in each essential oil.

Firstly, referring to FIG. 1a, it can be seen that porous silica is a spherical particle having a fine size and has a number of pores formed on the surface. Porous silica has a very large surface area due to the pores formed on the surface and has a three-dimensional skeleton structure, thereby loading essential oils efficiently. Preferably, the porous silica has an average diameter of 1 to 100 μm and a porosity of the particles of 80% or more. More preferably, the porous silica has an average diameter of 1 to 20 μm and a porosity of the particles of 90% or more.

Silica is a chemically stable material, but it is capable of detachment/attachment of desired functional groups to hydrophilic or hydrophobic functional groups on the silica surface. In particular, the hydrophilic or hydrophobic properties of the silica surface can be controlled by controlling functional groups by inducing surface adsorption/desorption or chemical reaction with water, acid, alkali and moisture in the atmosphere, carbon dioxide, and the like. Therefore, as the porous silica including a large amount of hydrophobic functional groups is heat-treated in an atmosphere containing oxygen or water vapor, the hydrophobic functional groups on the surface of the porous silica may be desorbed and replaced with hydrophilic functional groups such as —OH, thereby changing the atomic ratio between oxygen and carbon (O/C) of the porous silica. As such, the hydrophilicity or hydrophobicity can be controlled.

As can be seen from FIG. 2, there are various kinds of aromatic essential oils. The essential oils may be at least one of lavender, cinnamon leaf, tea tree, cedar wood, orange, eucalyptus, bergamot, lemon, lime, mandarin, myrrh, neroli, niaouli, peppermint, pine, rosemary, chamomile, ylang-ylang, neem, frankincense, benzoin, helichrysum or phytoncide.

It can be seen that chemical components included in therapeutic essential oil extracted from lavender, cinnamon leaf, tea tree, cedar wood, orange, eucalyptus or peppermint as shown in FIG. 2 contain a hydrophilic compound containing —OH and a hydrophobic compound consisting of C and H only, respectively.

The main components in each essential oil have different levels of polarity according to their chemical formula. When each of essential oils mainly contains a polar component, it may have hydrophilic properties. On the contrary, if the main components exhibit low polarity, it may have hydrophobic properties. Therefore, in the case of essential oils, hydrophilicity or hydrophobicity is determined by the type of each component. Accordingly, in order to load these essential oils and to impart loading stability, it is required to match the properties of the carrier to the properties of the essential oils.

Since the fragrant material according to the embodiment of the present invention is composed of spherical porous silica having a large number of pores, the essential oil can be efficiently loaded by adjusting the surface properties of the porous silica. In particular, it is possible to improve the loading affinity with the essential oil by adjusting the ratio (O/C) of oxygen and carbon on the surface of the porous silica through heat treatment in an atmosphere containing oxygen. As a result, it is possible to secure the intensity of aroma and the retention of smell for various kinds of aroma components of essential oil.

The aroma of essential oil is determined by volatile components contained in the essential oil and their composition ratio. In case of long-term fragrance, the characteristics of the smell may be different from that of the initial smell due to a change in composition ratio due to different volatility. Therefore, it is possible to make the initial smell of the essential oil last longer by allowing the sustained action on the volatile components.

The fragrant material having long-lasting fragrance according to the embodiment of the present invention may be heat-treated in a heating furnace in order to maintain the initial smell of the essential oil for a long time by controlling the surface properties of the porous silica.

More preferably, compared to a simple heat treatment, the heat treatment of the porous silica in a heating furnace equipped with a device capable of actively supplying oxygen or water vapor facilitates control of the oxygen and carbon ratio (O/C) on the surface of the porous silica.

The main components of essential oil may vary depending on the type of the essential oil. With consideration of aroma intensity (smell intensity) and the retention of the initial aroma (initial aroma retention), it is preferable that the essential oil to be loaded and porous silica satisfy the following condition:

$$0.9 \leq rHLB \text{ (required Hydrophilic-lipophilic balance)}$$
$$\text{of essential oil}/(O/C \text{ ratio of porous silica}) \leq 2.9$$

If the rHLB (required Hydrophilic-lipophilic balance) of essential oil/(O/C ratio of porous silica) is less than 0.9 or greater than 2.9, that is, if the polarity difference between the essential oil and the carrier is great, the essential oil is not reliably loaded on the carrier, or essential oil after loading is re-released to the outside of the porous silica, so that the degree of aggregation or the viscosity of the porous silica becomes very high and thus the loading stability may be significantly lowered. If the loading stability is low, it may be difficult to maintain the initial aroma over time.

Therefore, in the fragrant material having long-lasting fragrance according to the embodiment of the present invention, the heat treatment process of the porous silica may be performed as follows.

That is, the heat treatment process may comprise the steps of: injecting the porous silica into a heating furnace; heat-treating for about 1 hour to 3 hours while maintaining the temperature of the heating furnace at about 100 to 550° C.; and cooling the heat-treated porous silica to 25° C.

When the porous silica is subjected to heat treatment for less than about 1 hour at a temperature of less than about 100° C., the carbon on the surface of the porous silica and the supplied oxygen are difficult to bond sufficiently. On the other hand, silica is a relatively stable material, but the heat treatment for more than about 3 hours under temperature conditions exceeding about 550° C. causes serious evaporation of C present in the porous silica, making it difficult to control O/C ratio of the porous silica. In consideration of this, it is preferable that the porous silica is heat treated for about 1 hour to 3 hours at about 100 to 550° C.

The above process can provide a carrier for long-term fragrance including porous silica having an O/C weight ratio of about 3 to 15.

The heat treatment process may further comprise supplying oxygen, water vapor, or a mixture thereof. By actively supplying oxygen, water vapor or a mixture thereof, the O/C ratio of the entire surface of the porous silica may be uniformly formed to facilitate the control of O/C ratio.

In addition, when only oxygen is supplied in the heat treatment process, the reaction stability may be lowered. Therefore, it is preferable to supply water vapor together.

The fragrant material having long-lasting fragrance according to the embodiment of the present invention may further comprise an additional carrier which is formed of at least one of a polymer material such as silicone, rubber, plastic and urethane, clay and gypsum.

The additional carrier may be mixed with the essential oil-loaded porous silica or used as a material for coating the porous silica.

In the process of mixing or coating with the additional carrier and then curing or drying, it is possible to manufacture in a design having a shape desired by a user or a consumer. A method of spraying, microencapsulation, or blade coating may be used for coating. Of course, the method of curing or coating is not limited to the method illustrated above.

Therethrough, materials including essential oils for long-lasting fragrance in accordance with the embodiment of the present invention can be made into products of various shapes and designs, which can be applied to various ornaments or accessories for aromatherapy of not only people but also pets.

Hereinafter, loading stability of the essential oil of the fragrant material having long-lasting fragrance according to the embodiment of the present invention will be described.

Figure 3:
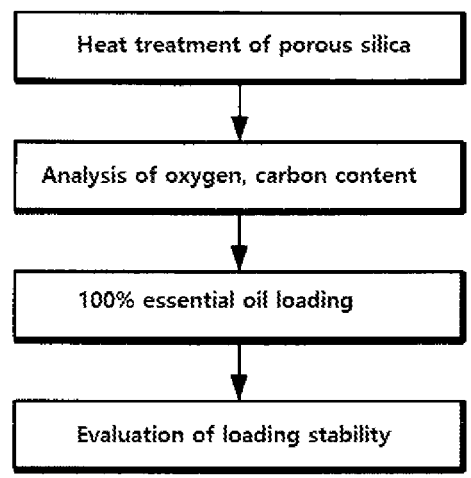
FIG. 3 is a flowchart showing a method of proceeding in Comparative Examples and Examples of the present invention.

FIG. 3 is a flowchart showing a method of proceeding in Comparative Examples and Examples of the present invention.

Comparative Example and Example of the present invention proceeded as shown in FIG. 3.

1. Test for Controlling of Oxygen/Carbon (O/C) Ratio of Porous Silica

The heat treatment of porous silica for loading stability test of the essential oil (100% essential oil) was performed as shown in Table 2.

TABLE 2

Heat treatment method of porous silica and analysis method of oxygen/carbon (O/C) content for loading stability test of aromatic essential oil (100% essential oil)

|  |  | Type of porous silica | Experiment method for porous silica-1, -2, -3 |
|---|---|---|---|
| Comp. Ex. | 1-1 | Porous silica-1 | (Manufacturing method of porous silica-1) 1. Take about 100 g of porous silica. |
|  | 1-2 | Porous silica-3 | 2. Putting in a heating furnace equipped with oxygen and water vapor supplying unit. |
|  | 2-1 | Porous silica-1 | 3. Increase the temperature of the heating furnace to about 350° C. while introducing |
|  | 2-2 | Porous silica-3 | an oxygen source containing water vapor via the oxygen and water vapor supplying unit. |
|  | 3-1 | Porous silica-3 | 4. Heat treating at about 350° C. for about 2 hours. |
|  | 4-1 | Porous silica-1 | 5. Cool to room temperature (about 25° C.). 6. Take a sample at room temperature. |
|  | 5-1 | Porous silica-1 | 7. Measure C content (carbon content) with a carbon analyzer/Measure O content |
|  | 6-1 | Porous silica-1 | (oxygen content) with an oxygen analyzer. (Manufacturing method of porous silica-2) |
|  | 6-2 | Porous silica-3 | 1. Take about 100 g of porous silica. 2. Putting in a heating furnace equipped with |
|  | 7-1 | Porous silica-1 | oxygen and water vapor supplying unit. 3. Increase the temperature of the heating |
|  | 7-2 | Porous silica-3 | furnace to about 400° C. while introducing an oxygen source containing water vapor via |
| Ex. | 1-1 | Porous silica-2 | the oxygen and water vapor supplying unit. 4. Heat treating at about 400° C. for about |
|  | 2-1 | Porous silica-2 | 2 hours. 5. Cool to room temperature (about 25° C.). |
|  | 3-1 | Porous silica-1 | 6. Take a sample at room temperature. |
|  | 3-2 | Porous silica-2 | 7. Measure C content (carbon content) with a carbon analyzer/Measure O content |
|  | 4-1 | Porous silica-2 | (oxygen content) with an oxygen analyzer. (Manufacturing method of porous silica-3) |
|  | 4-2 | Porous silica-3 | 1. Take about 100 g of porous silica. 2. Putting in a heating furnace equipped with |
|  | 5-1 | Porous silica-2 | oxygen and water vapor supplying unit. 3. Increase the temperature of the heating |
|  | 5-2 | Porous silica-3 | furnace to about 500° C. while introducing an oxygen source containing water vapor via |
|  | 6-1 | Porous silica-2 | the oxygen and water vapor supplying unit. 4. Heat treating at about 500° C. for about |
|  | 7-1 | Porous silica-2 | 2 hours. 5. Cool to room temperature (about 25° C.). 6. Take a sample at room temperature. 7. Measure C content (carbon content) with a carbon analyzer/Measure O content (oxygen content) with an oxygen analyzer. |

2. Test for Loading Aromatic Essential Oil (100% Essential Oil) on Porous Silica having Controlled Oxygen/Carbon (O/C) Ratio Various kinds of essential oils (100% essential oils) were loaded on porous silica having controlled oxygen/carbon (O/C) ratio according to the method shown in Table 3.

TABLE 3

Experimental method for loading essential oil on heat-treated porous silica

|  |  | Type of porous silica | Loaded essential oil | Experimental method for loading essential oil |
|---|---|---|---|---|
| Comp. Ex. | 1-1 | Porous silica-1 | Lavender | 1. Take 2 g of heat treated porous silica (-1, -2, -3). |
|  | 1-2 | Porous silica-3 | Lavender | 2. Put it in a 70 ml vial. |
|  | 2-1 | Porous silica-1 | Cinnamon Leaf | 3. Add 6 g of a desired |
|  | 2-2 | Porous silica-3 | Cinnamon Leaf | essential oil (100% |
|  | 3-1 | Porous silica-3 | Tea Tree | essential oil) to the vial. |
|  | 4-1 | Porous silica-1 | Cedar Wood | 4. Place mixing balls into |
|  | 5-1 | Porous silica-1 | Orange | the vial and mix for |
|  | 6-1 | Porous silica-1 | Eucalyptus | 4 hours at about 100 rpm |
|  | 6-2 | Porous silica-3 | Eucalyptus | with a rolling-machine. |
|  | 7-1 | Porous silica-1 | Peppermint | 5. Recover the sample |
|  | 7-2 | Porous silica-3 | Peppermint | 6. Evaluate according |
| Ex. | 1-1 | Porous silica-2 | Lavender | to criteria of loading |
|  | 2-1 | Porous silica-2 | Cinnamon Leaf | stability of essential oil. |
|  | 3-1 | Porous silica-1 | Tea Tree | 7. Calculate loading |
|  | 3-2 | Porous silica-2 | Tea Tree |  |

TABLE 3-continued

Experimental method for loading essential oil on heat-treated porous silica

| | Type of porous silica | Loaded essential oil | Experimental method for loading essential oil |
|---|---|---|---|
| 4-1 | Porous silica-2 | Cedar Wood | amount of essential oil by weighing the sample. |
| 4-2 | Porous silica-3 | Cedar Wood | |
| 5-1 | Porous silica-2 | Orange | |
| 5-2 | Porous silica-3 | Orange | |
| 6-1 | Porous silica-2 | Eucalyptus | |
| 7-1 | Porous silica-2 | Peppermint | |

3. Test for Loading Stability of Essential Oil-Loaded Porous Silica Material

Figure 4:
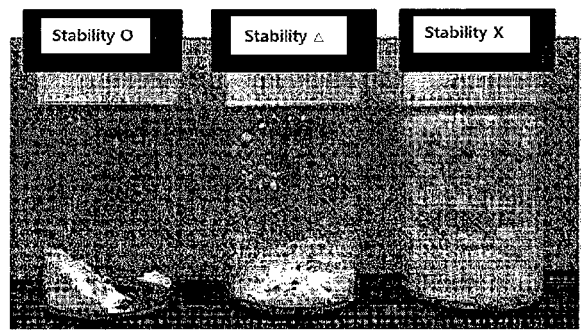
FIG. 4 shows the degree of aggregation of particles on the inner wall of the vial.

Loading stability of the porous silica material loading essential oil was determined by the degree of aggregation of particles on the inner wall of the vial as shown in Table 4 and FIG. 4, after loading the essential oil on the porous silica.

FIG. 4 shows the degree of aggregation of particles on the inner wall of the vial.

TABLE 4

Criteria for determination of loading stability of essential oil-loaded porous silica particles

| Criteria | Stability |
|---|---|
| After loading the essential oil, almost no particles agglomerate on the inner wall of the vial. | O |
| After loading the essential oil, small amount of particles aggregate on the inner wall of the vial is observed. | Δ |
| After loading the essential oil, the particles agglomerate on the inner wall of the vial and there is no particle flow. | X |

4. Evaluation Results of Loading Stability of Essential Oil 4-1. Table 5 Shows the Measurement Results of Oxygen/Carbon (O/C) Ratio of Porous Silica After Heat Treatment.

TABLE 5

Measurement results of oxygen/carbon (O/C) ratio of porous silica after heat treatment.

| Carrier | Porous silica-1 | Porous silica-2 | Porous silica-3 |
|---|---|---|---|
| Oxygen content (wt %) | 38.5 | 48.6 | 52.5 |
| Carbon content (wt %) | 12.4 | 5.8 | 3.5 |
| Oxygen/carbon (O/C) ratio | 3.1 | 8.4 | 15.0 |

As can be seen in Table 5, when the porous silica is heat-treated under the temperature and atmosphere condition as described above, the oxygen/carbon (O/C) ratio can be controlled to 3 to 15. As a result, the hydrophilicity or hydrophobicity of the porous silica can be controlled.

4-2. Loading Stability of Essential Oil According to the rHLB (Required Hydrophilic-Lipophilic Balance) of Essential Oil and the Ratio of Oxygen/Carbon (O/C)

From the main components of the various essential oils (100% essential oil) and rHBL value shown in FIG. 2, the results of loading stability test shown in Table 4, and the measurement results of oxygen/carbon (O/C) ratio of porous silica after heat treatment shown in Table 5, it can be seen that (rHLB of essential oil)/(O/C ratio of porous silica) affects the loading stability depending on the type of essential oil. This is summarized in Table 6.

TABLE 6

Effect of (rHLB of essential oil)/(O/C ratio of porous silica) on loading stability of essential oil

| Type of essential oil | Loading ratio of essential oil/silica | Loading stability of essential oil | | | rHLB of essential oil | Porous silica-1 | Porous silica-2 | Porous silica-3 |
| | | Porous silica-1 | Porous silica-2 | Porous silica-3 | | | | |
|---|---|---|---|---|---|---|---|---|
| Lavender | 3 | x | o | Δ | 12.0 | 3.9 | 1.4 | 0.8 |
| Cinnamon Leaf | 3 | x | o | Δ | 11.1 | 3.6 | 1.3 | 0.7 |
| Tea Tree | 3 | o | o | x | 9.0 | 2.9 | 1.1 | 0.6 |
| Cedar Wood | 3 | x | o | o | 16.7 | 5.4 | 2.0 | 1.1 |
| Orange | 3 | x | o | o | 13.0 | 4.2 | 1.5 | 0.9 |
| Eucalyptus | 3 | Δ | o | Δ | 9.8 | 3.2 | 1.2 | 0.7 |
| Peppermint | 3 | x | o | Δ | 12.3 | 4.0 | 1.5 | 0.8 |

Referring to Table 6 above, which summarizes the results of Examples and Comparative Examples of the present invention, it can be seen that the loading stability of the desired essential oil (100% essential oil) can be ensured only with porous silica having an oxygen/carbon (O/C) ratio (hydrophilic or hydrophobic property) within an appropriate range. That is, in order to load various kinds of aromatic essential oil, it is necessary to control the oxygen/carbon (O/C) ratio of the carrier (porous silica) preferentially.

From Table 6, it can be seen that when the rHLB of the essential oil to be loaded and the O/C ratio in the porous silica satisfy the following equation, there is excellent loading stability.

$$0.9 \leq \text{required hydrophilic-lipophilic balance (rHLB)} \text{ of essential oil}/(\text{O/C ratio of porous silica}) \leq 2.9.$$

5. Sample Preparation for Evaluation Test of Fragrance Sensory and Retention of Materials Loading Essential Oil (100% Essential Oil)

In the example of the present invention, the fragrant material (primary carrier) comprising essential oil having about 3:1 weight ratio of essential oil (100% essential oil) to porous silica having controlled oxygen/carbon (O/C) ratio was prepared, and the material was mixed with silicone, clay or gypsum to prepare a molded product (dual carrier). In addition, for the comparative example, a molded product of mixture of essential oil and silicone, a molded product of mixture of essential oil and clay, and a molded product of mixture of essential oil and gypsum were prepared, and the fragrance sensory evaluation of each of these samples was performed.

Comparative Example 8: Sensory Test of Lavender Essential Oil (100% Essential Oil)

0.5 g of lavender is placed in a 70 ml vial, and the evaluation is carried out according to the fragrance sensory evaluation method.

Example 8: Sensory Test of Fragrant Material Comprising Lavender Essential Oil/Porous Silica-2 (Primary Carrier)

0.67 g of the sample prepared in Example 1-1 was placed in a 70 ml vial, and the evaluation was carried out according to the fragrance sensory evaluation method.
(Comparative Example 8 and Example 8 have the amount of lavender of 0.5 g, which are based on same content)

Comparative Example 9: Sensory Test of Molded Product of Mixture of Lavender Essential Oil and Silicone 1) 0.5 g of lavender essential oil is mixed with 2 g of silicone rubber stock solution.
2) The mixed solution is placed in the mold with a certain size, and then cured.
3) The molded product is put into a 70 ml vial and evaluated according to the fragrance sensory evaluation method.

Example 9: Sensory Test of Silicone Molded Product (Dual Silicone Carrier) of Lavender Essential Oil/Porous Silica-2 (Primary Carrier)

1) 0.67 g of the sample prepared in Example 1-1 is mixed with 2 g of silicone rubber stock solution.
2) The mixed solution is placed in the mold with a certain size, and then cured.
3) The molded product is put into a 70 ml vial and evaluated according to the fragrance sensory evaluation method.
(Comparative Example 9 and Example 9 have the amount of lavender of 0.5 g, which are based on same content)

Comparative Example 10: Sensory Test of Clay Molded Product of Lavender Essential Oil 1) 0.5 g of lavender is mixed with 2 g of clay.
2) The mixture is placed in the mold with a certain size, and then dried at room temperature for about 1 day.
3) The molded product is put into a 70 ml vial and evaluated according to the fragrance sensory evaluation method.

Example 10: Sensory Test of Clay Molded Product (Dual Clay Carrier) of Lavender Essential Oil/Porous Silica-2 Carrier 1) 0.67 g of the sample prepared in Example 1-1 is mixed with 2 g of clay.
2) The mixture is placed in the mold with a certain size, and then dried at room temperature for about 1 day.
3) The molded product is put into a 70 ml vial and evaluated according to the fragrance sensory evaluation method.
(Comparative Example 10 and Example 10 have the amount of lavender of 0.5 g, which are based on same content)

Comparative Example 11: Sensory Test of Gypsum Molded Product of Lavender Essential Oil 1) 0.5 g of lavender is mixed with 4 g of gypsum solution (2 g of gypsum and 2 g of water).
2) The mixture is placed in the mold with a certain size, and then dried at room temperature for about 1 day.
3) The molded product is put into a 70 ml vial and evaluated according to the fragrance sensory evaluation method.

Example 11: Sensory Test of Gypsum Molded Product (Dual Gypsum Carrier) of Lavender Essential Oil/Porous Silica-2 Carrier 1) 0.67 g of the sample prepared in Example 1-1 is mixed with 4 g of gypsum solution (2 g of gypsum and 2 g of water).
2) The mixture is placed in the mold with a certain size, and then dried at room temperature for about 1 day.
3) The molded product is put into a 70 ml vial and evaluated according to the fragrance sensory evaluation method.
(Comparative Example 11 and Example 11 have the amount of lavender of 0.5 g, which are based on same content)

6. Evaluation and Analysis Method of Fragrance Sensory and Retention of Initial Aroma of Materials Loading Essential Oil (100% Essential Oil)

6-1. Sample Preparation for Evaluation Test of Fragrance Sensory and Retention of Initial Aroma 1) Sample is prepared as in the Comparative Example and the Example.
: All samples have the same amount of essential oil content.
2) The sample prepared in 1) is added into a 70 ml vial.
3) An appropriate amount of purified water is placed in a 1 L beaker, and the temperature is raised on a hot plate set at about 50° C.
4) The vial containing the sample put in the 1 L beaker.
5) When it reaches 50° C., the lid of the sample is opened and left.
6) The sample is collected using a 1 L tether bag for a predetermined time (a period of standing).
7) The aroma intensity and the retention of initial aroma of the collected sample is evaluated by the panel trained for aroma according to the sensory evaluation criteria in the following table.

6-2. Evaluation Criteria for Fragrance Sensory Evaluation and Retention of Initial Aroma The fragrance sensory evaluation of the samples prepared in 6-1 is performed based on the criteria shown in Table 7, and the retention of initial aroma evaluation is performed based on the criteria shown in Table 8.

TABLE 7

| Evaluation criteria for fragrance level | |
|---|---|
| Fragrance level | Evaluation criteria |
| 0 | No smell |
| 1 | Aroma to feel slightly (minimum detection concentration) |
| 2 | Weak aroma to cognize what kind of aroma (minimum perception concentration) |
| 3 | Aroma to easily cognize |
| 4 | Irritating aroma |

TABLE 7-continued

Evaluation criteria for fragrance level

| Fragrance level | Evaluation criteria |
|---|---|
| 5 | Strong aroma |
| 6 | Intense aroma |
| 7 | Very irritating and intense aroma |

TABLE 8

Retention of initial aroma

| Initial aroma retention level | Evaluation criteria |
|---|---|
| 0 | A completely different kind of aroma |
| 1 | Grading the degree of aroma difference from the |
| 2 | initial aroma (The higher the number, the more |
| 3 | similar to initial aroma) |
| 4 | |
| 5 | Same as initial aroma |

7. Analysis and Evaluation Results of Fragrance Sensory and Retention of Initial Aroma of Materials Loading Essential Oils (100% Essential Oil)

Table 9 shows the results of test for aroma retention according to the above sensory evaluation for the material containing essential oil having long-lasting fragrance according to other embodiment of the present invention, in which lavender essential oil (100% essential oil) is applied to a dual carrier of porous silica-2 and silicone, clay or gypsum according to the above examples (Examples 8 to 11).

As can be seen from Table 9, for various dual carriers, it can be seen that the characteristics related to the aroma intensity and the initial smell retention are enhanced.

Figure 5:
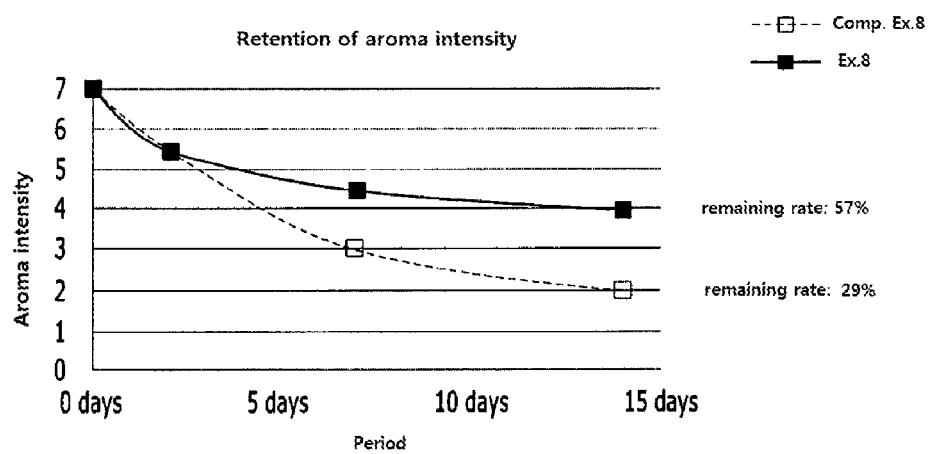
FIG. 5 is a graph showing the results of the retention of aroma intensity of Comparative Example 8 and Example 8.

FIG. 5 is a graph showing the results of the retention of aroma intensity of Comparative Example 8 and Example 8.

Figure 6:
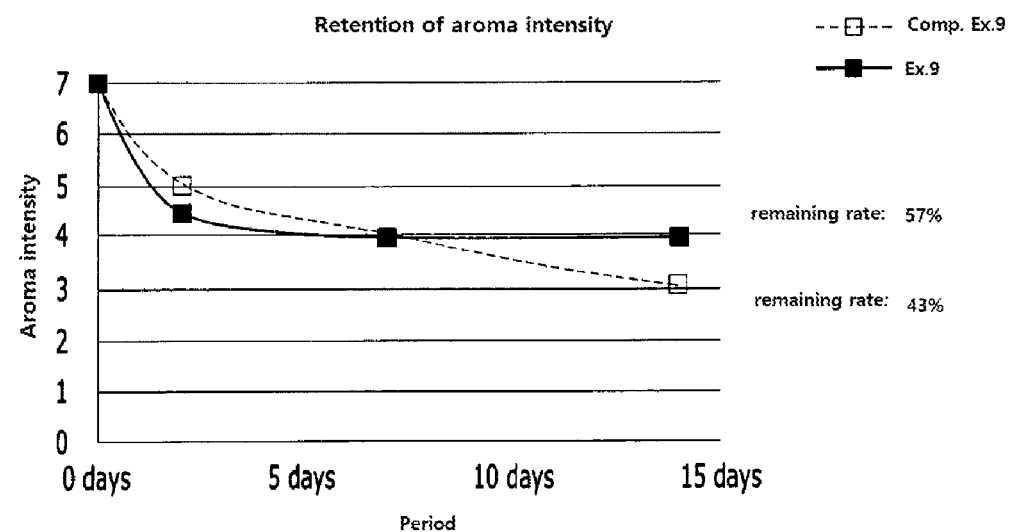
FIG. 6 is a graph showing the results of the retention of aroma intensity of Comparative Example 9 and Example 9.

FIG. 6 is a graph showing the results of the retention of aroma intensity of Comparative Example 9 and Example 9.

Figure 7:
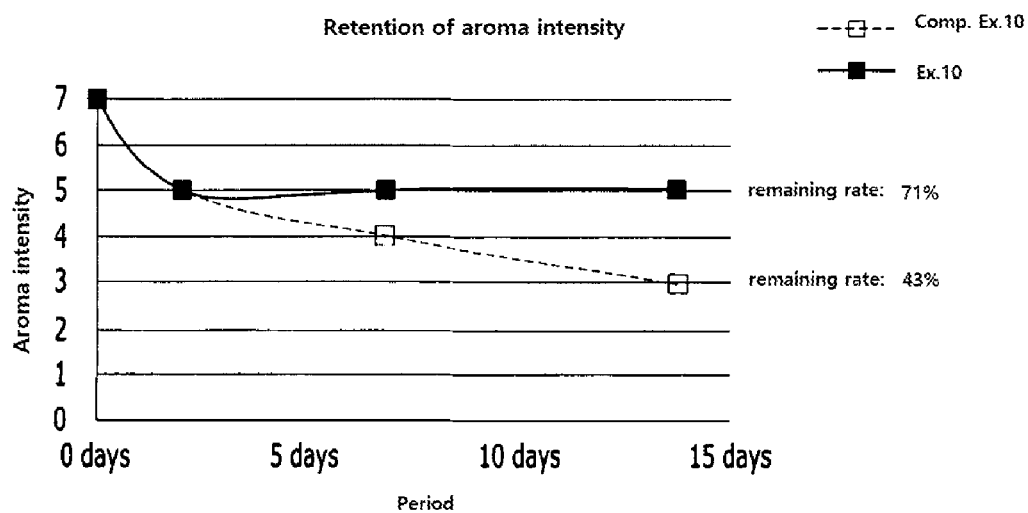
FIG. 7 is a graph showing the results of the retention of aroma intensity of Comparative Example 10 and Example 10.

FIG. 7 is a graph showing the results of the retention of aroma intensity of Comparative Example 10 and Example 10.

Figure 8:
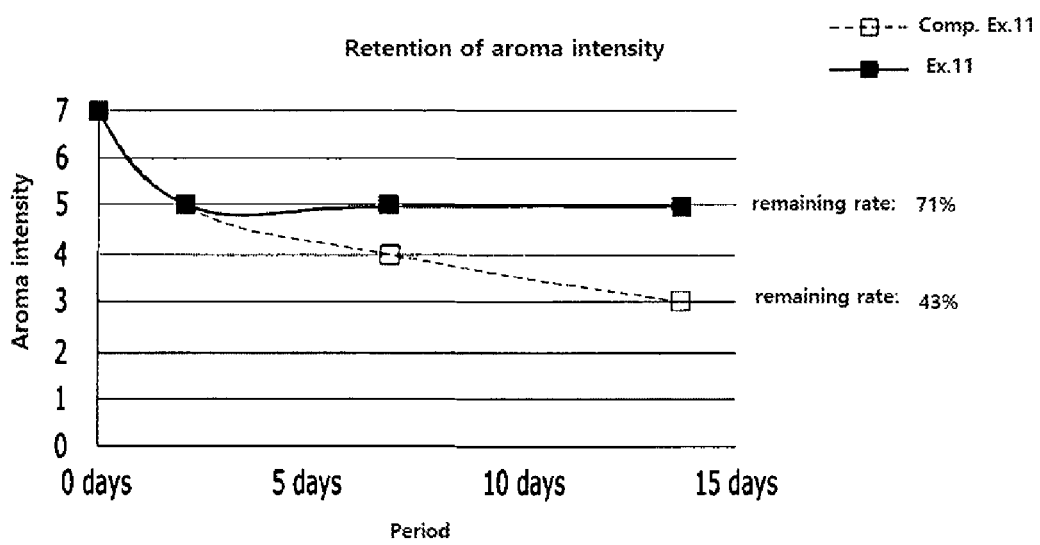
FIG. 8 is a graph showing the results of the retention of aroma intensity of Comparative Example 11 and Example 11.

FIG. 8 is a graph showing the results of the retention of aroma intensity of Comparative Example 11 and Example 11.

FIGS. 5 to 8 show that after a 14-day standing period, 100% lavender essential oil shows a remaining rate of about 29%, but in the case that lavender essential oil is loaded on the controlled porous silica according to an embodiment of the present invention, the remaining rate is about 57%, which indicates the retention of aroma intensity is greatly increased.

In addition, as can be seen in FIGS. 6, 7, and 8, it can be seen that when the primary carrier structure is applied, the remaining rate is significantly improved. Furthermore, as shown in FIGS. 7 and 8, when the molded product (dual carrier) is applied, the retention of aroma intensity is further improved as compared with the primary carrier structure depending on the substance (Remaining rate improved from 57% to 71%).

It means that control and retention of aroma can be further improved if the molded product is produced by selecting appropriate materials.

In general, aromatic essential oil (100% essential oil) is not composed of a single aroma component, but is composed of several or several dozen of aroma components. Since each of these aroma components has a different volatility, the initial aroma intensity as well as the type of aroma are changed as the period of standing becomes longer. Such a change in the type of aroma may be perceived by the user as being changed to a different aroma as the period of use

TABLE 9

Test for fragrance retention

| | Carrier/ Essential oil | Carrier ratio (wt/wt) | Dual carrier | Sensory evaluation of aroma intensity (@50° C.)✕The higher the number, the higher the aroma intensity | | | | Sensory evaluation of retention of initial aroma (@50° C.)✕The higher the number, the more similar to initial aroma | | | | |
|---|---|---|---|---|---|---|---|---|---|---|---|---|
| | | | | | | | | Smell intensity | | | | |
| | | | | 0 day | 2 days | 7 days | 14 days | remaining rate (%) (14 days/0 day*100) | 0 day | 2 days | 7 days | 14 days |
| Comp. Ex. 8 | None/lavender | 3 | None | 7 | 5.5 | 3 | 2 | 29% | 5 | 5 | 2 | 2 |
| Ex. 8 | Porous silica-2/ lavender | 3 | None | 7 | 5.5 | 4.5 | 4 | 57% | 5 | 5 | 5 | 5 |
| Comp. Ex.9 | None/lavender | 3 | Silicone | 7 | 5 | 4 | 3 | 43% | 5 | 4 | 3 | 3 |
| Ex.9 | Porous silica-2/ lavender | 3 | Silicone | 7 | 4.5 | 4 | 4 | 57% | 5 | 5 | 5 | 5 |
| Comp. Ex. 10 | None/lavender | 3 | Clay | 7 | 5 | 4 | 3 | 43% | 5 | 3 | 3 | 3 |
| Ex. 10 | Porous silica-2/ lavender | 3 | Clay | 7 | 5 | 5 | 5 | 71% | 5 | 5 | 5 | 5 |
| Comp. Ex. 11 | None/lavender | 3 | Gypsum | 7 | 5 | 4 | 3 | 43% | 5 | 4 | 3 | 3 |
| Ex. 11 | Porous silica-2/ lavender | 3 | Gypsum | 7 | 5 | 5 | 5 | 71% | 5 | 5 | 5 | 4 | becomes longer. Furthermore, it may reduce or eliminate the physical and mental therapeutic effects of essential oils. Therefore, it is very important to monitor the retention of initial aroma.

Figure 9:
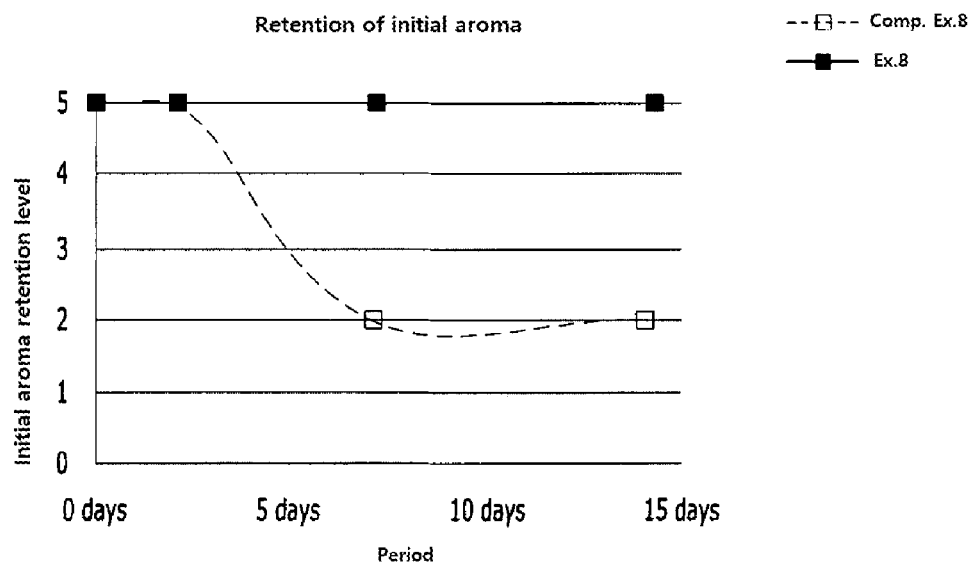
FIG. 9 is a graph showing the retention of initial aroma of Comparative Example 8 and Example 8.

FIG. 9 is a graph showing the retention of initial aroma of Comparative Example 8 and Example 8.

Figure 10:
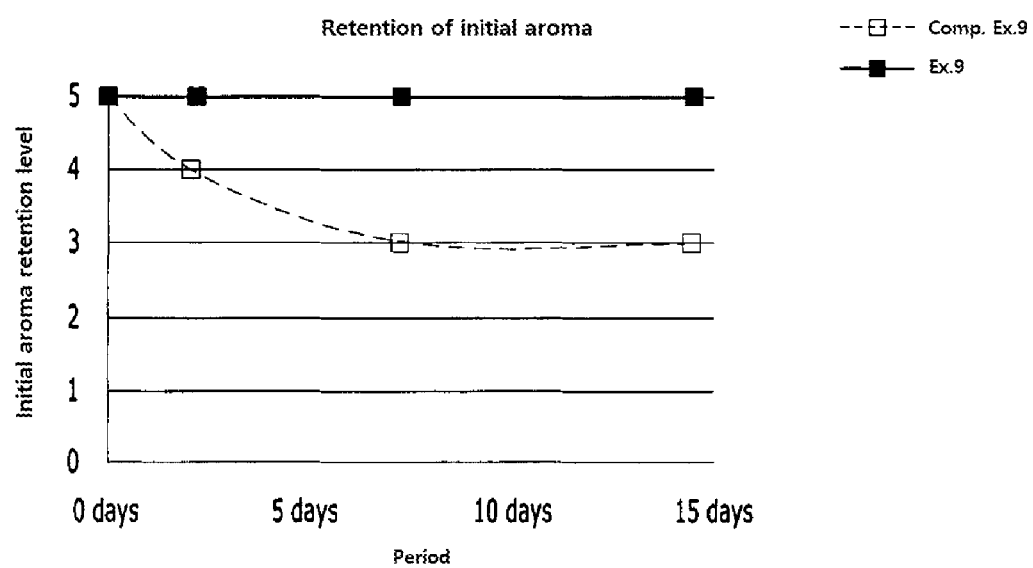
FIG. 10 is a graph showing the retention of initial aroma of Comparative Example 9 and Example 9.

FIG. 10 is a graph showing the retention of initial aroma of Comparative Example 9 and Example 9.

Figure 11:
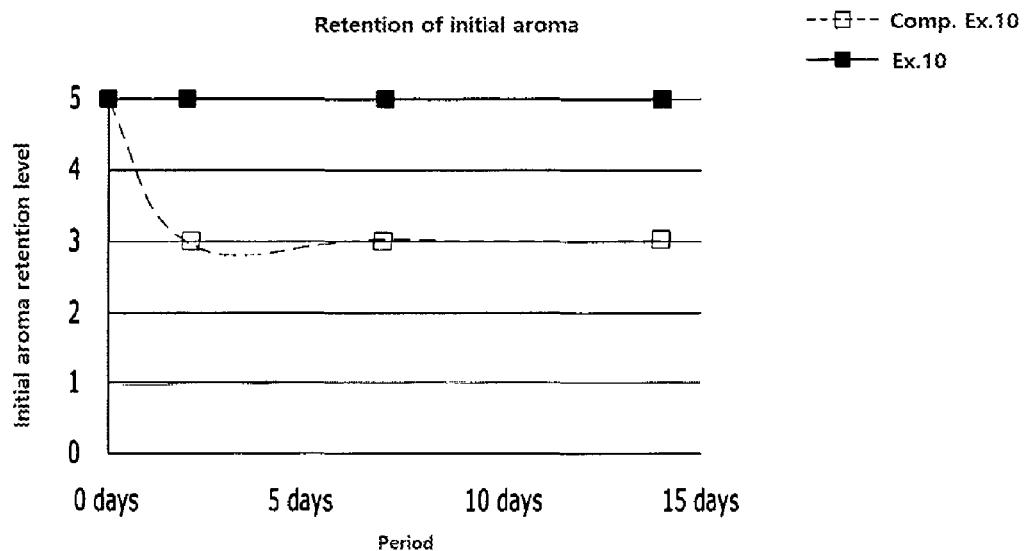
FIG. 11 is a graph showing the retention of initial aroma of Comparative Example 10 and Example 10.

FIG. 11 is a graph showing the retention of initial aroma of Comparative Example 10 and Example 10.

Figure 12:
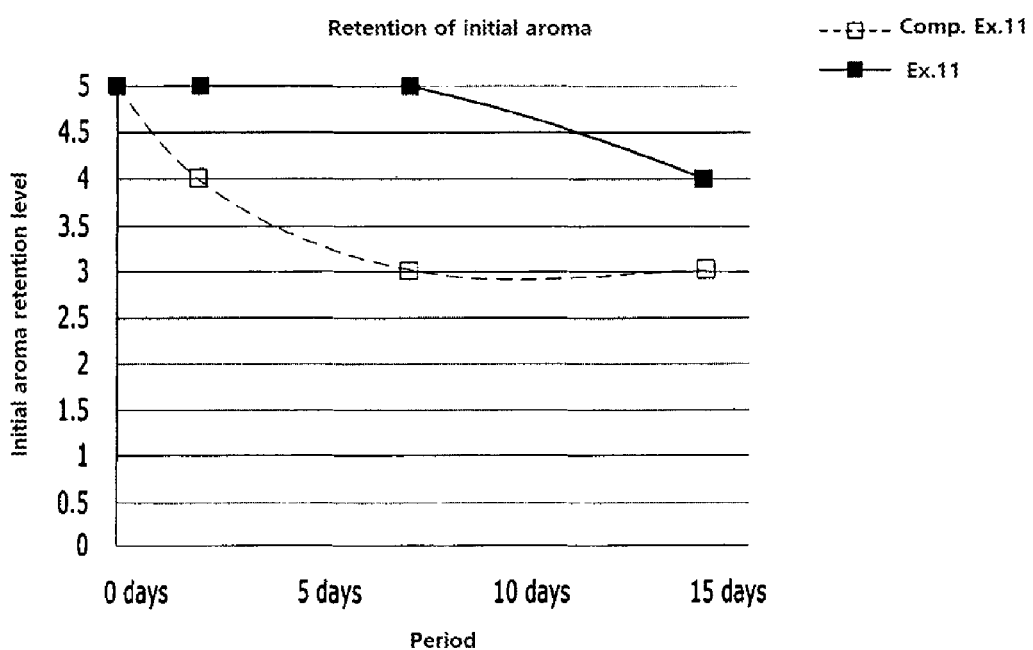
FIG. 12 is a graph showing the retention of initial aroma of Comparative Example 11 and Example 11.

FIG. 12 is a graph showing the retention of initial aroma of Comparative Example 11 and Example 11.

In the case of the sample prepared in Comparative Example 8, it can be seen that after 14-day standing period, the initial aroma was changed to another type. This is believed to be due to the volatilization of a relatively high volatile component among various volatile components included in lavender essential oil. However, in contrast, the sample of Example 8 prepared according to the embodiment of the present invention exhibited excellent characteristics that the initial aroma was maintained even after 14 days of standing. Therefore, it can be concluded that the retention of initial aroma is excellent in the case of the material including essential oil prepared by the embodiment of the present invention.

As can be seen in FIGS. 10, 11, and 12, when a molded product of mixture of lavender essential oil and a molding material is used, the initial aroma retention level slightly improves (2→3) compared to the lavender essential oil alone. However, when a molded product (dual carrier) is manufactured using a material including essential oil of the present invention, the initial aroma remains unchanged after 14 days of standing.

Therefore, it can be concluded that the configuration of the fragrant material (primary carrier) including the essential oil prepared according to the embodiment of the present invention plays a very large role in maintaining the persistence of the aroma intensity and the retention of initial aroma.

On the other hand, in the case of a material containing essential oil for long-lasting fragrance of the present invention has a great advantage in a variety of applications that can be used in aromatherapy of pets.

In order to improve or treat the physical and mental condition of animals, aromatic essential oil, that is, 100% essential oils, should be used. Artificial flavors and additives are known to harm animal health. Furthermore, in animals, even 100% essential oils, which are beneficial to humans, are known to cause great harm to the physical and mental health of animals because animals have different ability to decompose flavors in the liver from than humans. Therefore, it is required to take great caution to use. In addition, animals are known to be 50-100 times more sensitive to aroma than humans, and highly concentrated 100% essential oils cannot be used as they are.

Until now, for aromatherapy of pets, products are mainly used that diluted oils were applied directly to the skin, aroma oils are dropped into aroma candle or water to generate vapor, or sprayed onto a floor or pet goods.

However, applying diluted oil directly to the skin may cause skin troubles so that it requires extreme caution and leads to the limited usage.

In addition, in the conventionally used method of generating vapor in aroma candle or dispersed oil or spraying aroma, it is inconvenient to control the concentration of the aroma to the aroma-sensitive pet and it has an inconvenience in use because of the limited retention time.

Moreover, aroma candles have a fire hazard, and sprays are not available for pets that are alone without their guardians because of the risk of pet licking. In particular, if the guardian lives alone, the pets have a lot of time to be absolutely alone, and there is an absolute need for ways to alleviate emotional anxiety and stress.

Therefore, in order to improve and enhance the physical and mental health of animals using aromatic essential oil, 1) concentration, 2) retention time, 3) elimination of potential hazards, and 4) convenience of use with improved space and time constraints should be more carefully and delicately controlled.

It is possible to control the concentration and fragrance retention of the aromatic essential oil, by loading essential oil in a porous silica containing essential oil for long-lasting fragrance according to the embodiment of the present invention as described above to confine aroma and by adjusting a ratio of a carrier and loaded oil and a ratio of a molding material (polymer such as silicone, urethane and plastic, gypsum and clay) and a fragrant material including essential oil for long-lasting fragrance of the present invention. In addition, the retention of initial aroma is very high, which can further impart efficiency and convenience of use.

When molding material such as polymers such as silicone, urethane and plastic, gypsum and clay are used to prepare a dual carrier, various shapes can be implemented such that they can be used safely and comfortably and can also be used in the form of accessories to be attached to human body or pet's body.

In the present specification and drawings, preferred embodiments of the present invention have been disclosed, and although specific terms have been used, these are merely used in a general sense to easily explain the technical contents of the present invention and to help the understanding of the present invention and are not intended to limit the scope. It will be apparent to those skilled in the art that other modifications based on the technical idea of the present invention can be carried out in addition to the embodiments disclosed herein.

What is claimed is:

1. A fragrant material having long-lasting fragrance, comprising:
an aromatic essential oil; and
porous silica for loading the aromatic essential oil, the porous silica having a surface with a controlled hydrophilicity or hydrophobicity,
wherein a required hydrophilic-lipophilic balance (rHLB) of the aromatic essential oil and an atomic ratio between oxygen/carbon (O/C ratio) in the porous silica satisfy the following condition:

$$0.9 \leq \text{required hydrophilic-lipophilic balance (rHLB)} \text{ of aromatic essential oil}/(\text{O/C ratio of porous silica}) \leq 2.9.$$

2. The fragrant material having long-lasting fragrance according to claim 1, wherein the porous silica is heat-treated under an atmosphere containing at least one of oxygen and water vapor.

3. The fragrant material having long-lasting fragrance according to claim 2, wherein the heat-treating is conducted by a process comprising the steps of: injecting the porous silica into a heating furnace; heat-treating for about 1 hour to 3 hours while maintaining the temperature of the heating furnace at about 100 to 550° C.; and cooling the heat-treated porous silica to 25° C.

4. The fragrant material having long-lasting fragrance according to claim 1, wherein the fragrant material further comprises an additional carrier formed of at least one of a polymer material, clay and gypsum.

5. The fragrant material having long-lasting fragrance according to claim 4, wherein the additional carrier is mixed with the porous silica or coated on the porous silica.

6. The fragrant material having long-lasting fragrance according to claim 5, wherein the fragrant material is formed by mixing or coating the porous silica with the additional carrier, and then curing or drying according to a predetermined design.

7. The fragrant material having long-lasting fragrance according to claim 4, wherein the polymer material is at least one of silicone, rubber, plastic, urethane, and a combination thereof.

8. A fragrant product having long-lasting fragrance, comprising:
    an aromatic essential oil;
    the porous silica for loading the aromatic essential oil, the porous silica having a surface with a controlled hydrophilicity or hydrophobicity; and
    purified water, the aromatic essential oil loaded in the porous silica being mixed with the purified water or dispersed in the purified water; wherein a required hydrophilic-lipophilic balance (rHLB) of the aromatic essential oil and an atomic ratio between oxygen/carbon (O/C ratio) in the porous silica satisfy the following condition:

$$0.9 < \text{required hydrophilic-lipophilic balance ((HLB)} \\ \text{of aromatic essential oil}/(\text{O/C ratio of porous} \\ \text{silica}) < 2.9.$$

9. The fragrant product having long-lasting fragrance according to claim 8, wherein the porous silica is heat-treated under an atmosphere containing at least one of oxygen and water vapor.

10. The fragrant product having long-lasting fragrance according to claim 9, wherein the heat-treating is conducted by a process comprising the steps of:
    injecting the porous silica into a heating furnace;
    heat-treating for about 1 hour to 3 hours while maintaining the temperature of the heating furnace at about 100 to 550° C.; and
    cooling the heat-treated porous silica to 25° C.

11. The fragrant product having long-lasting fragrance according to claim 8, wherein the fragrant product further comprises an additional carrier formed of at least one of a polymer material, clay and gypsum.

12. The fragrant product having long-lasting fragrance according to claim 11, wherein the additional carrier is mixed with the porous silica or coated on the porous silica.

13. The fragrant product having long-lasting fragrance according to claim 11, wherein the polymer material is at least one of silicone, rubber, plastic, urethane, and a combination thereof.

14. The fragrant product having long-lasting fragrance according to claim 8, wherein the fragrant product is at least one of an aromatic spray, an aromatic liquid product, a detergent/cleansing, a body care product, a hair care product and a pet care product.

15. A method of preparing a fragrant material having long-lasting fragrance, comprising the steps of:
    heat-treating porous silica to adjust hydrophilicity or hydrophobicity of a surface thereof, and
    mixing an aromatic essential oil with the heat-treated porous silica to load therein,
    wherein a required hydrophilic-lipophilic balance (rHLB) of the aromatic essential oil and an atomic ratio between oxygen and carbon (O/C ratio) in the porous silica satisfy the following condition:

$$0.9 \leq \text{required hydrophilic-lipophilic balance (rHLB)} \\ \text{of aromatic essential oil}/(\text{O/C ratio of porous} \\ \text{silica}) \leq 2.9.$$

16. The method of preparing a fragrant material having long-lasting fragrance according to claim 15, wherein the heat-treating proceeds under an atmosphere containing at least one of oxygen and water vapor.

17. The method of preparing a fragrant material having long-lasting fragrance according to claim 16, wherein the heat-treating comprises the steps of:
    injecting the porous silica into a heating furnace;
    heat-treating for about 1 hour to 3 hours while maintaining the temperature of the heating furnace at about 100 to 550° C.; and
    cooling the heat-treated porous silica to 25° C.

18. The method of preparing a fragrant material having long-lasting fragrance according to claim 15, wherein the method further comprises a step of mixing or coating the porous silica with an additional carrier formed of at least one of a polymer material, clay and gypsum.

19. The method of preparing a fragrant material having long-lasting fragrance according to claim 18, wherein the method further comprises a step of producing fragrant applications by mixing or coating the porous silica with the additional carrier, and then curing or drying according to a predetermined design.

* * * * *